(12) United States Patent
Lisogurski (10) Patent No.: US 9,220,409 B2
(45) Date of Patent: Dec. 29, 2015

(54) OPTICAL INSTRUMENT WITH AMBIENT LIGHT REMOVAL

(75) Inventor: Daniel Lisogurski, Boulder, CO (US)

(73) Assignee: Covidien LP, Mansfield, MA (US)

( * ) Notice: Subject to any disclaimer, the term of this patent is extended or adjusted under 35 U.S.C. 154(b) by 778 days.

(21) Appl. No.: 13/484,808

(22) Filed: May 31, 2012

(65) Prior Publication Data

US 2013/0324811 A1 Dec. 5, 2013

(51) Int. Cl.
| | |
|---|---|
| *A61B 5/1455* | (2006.01) |
| *A61B 5/00* | (2006.01) |
| *A61B 5/0205* | (2006.01) |
| *A61B 5/024* | (2006.01) |
| *A61B 5/08* | (2006.01) |

(52) U.S. Cl.
CPC . *A61B 5/00* (2013.01); *A61B 5/024* (2013.01); *A61B 5/0205* (2013.01); *A61B 5/08* (2013.01); *A61B 5/1455* (2013.01); *A61B 5/14551* (2013.01); *A61B 5/7203* (2013.01); *A61B 5/7225* (2013.01)

(58) Field of Classification Search
CPC ............. A61B 5/1455; A61B 5/14551; A61B 5/14552; A61B 5/7203; A61B 5/7225
See application file for complete search history.

(56) References Cited

U.S. PATENT DOCUMENTS

| | | | |
|---|---|---|---|
| 4,758,119 A | 7/1988 | Frase et al. | |
| 4,773,422 A | 9/1988 | Isaacson et al. | |
| 4,781,195 A | 11/1988 | Martin | |
| 4,807,630 A | 2/1989 | Malinouskas | |
| 4,846,183 A | 7/1989 | Martin | |
| 4,911,167 A * | 3/1990 | Corenman et al. | 600/324 |
| RE33,643 E | 7/1991 | Isaacson et al. | |
| 5,193,543 A | 3/1993 | Yelderman | |
| 5,368,224 A | 11/1994 | Richardson et al. | |
| 5,533,507 A | 7/1996 | Potratz | |
| 5,934,277 A | 8/1999 | Mortz | |
| 5,954,644 A | 9/1999 | Dettling et al. | |
| 5,995,859 A | 11/1999 | Takahashi | |
| 6,229,856 B1 | 5/2001 | Diab et al. | |
| 6,381,479 B1 | 4/2002 | Norris | |
| 6,397,092 B1 | 5/2002 | Norris et al. | |
| 6,829,496 B2 | 12/2004 | Nagai et al. | |
| 7,190,985 B2 | 3/2007 | Petersen et al. | |

(Continued)

FOREIGN PATENT DOCUMENTS

| | | |
|---|---|---|
| EP | 1709902 A2 | 10/2006 |
| EP | 1916767 A1 | 4/2008 |
| WO | WO 2005/009221 | 2/2005 |

OTHER PUBLICATIONS

International Search Report and Written Opinion of the International Authority for application No. PCT/US2013/043324, mailed on Sep. 12, 2013.

*Primary Examiner* — Eric Winakur
(74) *Attorney, Agent, or Firm* — Shvarts & Leiz LLP (57) ABSTRACT

Processing circuitry may process a physiological signal such as a light signal attenuated by a subject. The physiological signal may include a desired component and an undesired component. A first filtering operation may be performed to remove at least a portion of the undesired component and a second filtering operation may be performed to reduce an undesired distortion introduced by the first filter. The transfer function of the second filter may be substantially the inverse of the transfer function of the first filter. One or more physiological parameters may be determined based on the filtered physiological signal.

21 Claims, 8 Drawing Sheets

(56) References Cited

U.S. PATENT DOCUMENTS

| | | |
|---|---|---|
| 7,221,971 B2 | 5/2007 | Diab et al. |
| 2006/0092328 A1 | 5/2006 | Anderson et al. |
| 2006/0161057 A1 | 7/2006 | Weber et al. |
| 2009/0182211 A1 | 7/2009 | Diab et al. |

\* cited by examiner

OPTICAL INSTRUMENT WITH AMBIENT LIGHT REMOVAL

The present disclosure relates to processing physiological signals More particularly, the present disclosure relates to processing photoplethysmography signals, comprising light signals attenuated by a subject, to remove ambient light.

SUMMARY

Systems and method are provided for processing a physiological signal. The physiological signal may comprise a light signal attenuated by a subject. The physiological signal may include a first component corresponding to a desired component and a second component corresponding to an undesired component. A first filtering operation may be performed to remove at least a portion of the undesired component using a first filter having a first transfer function to generate a first filtered signal. In some embodiments, the undesired component may comprise ambient light noise. In such embodiments, the first filter may be a high pass filter that brings the signal level to within the dynamic range of an analog-to-digital converter. A second filtering operation may be performed using a second filter having a second transfer function to generate a second filtered signal.

In some embodiments, the first filtering operation may introduce a distortion (e.g., an overshoot or droop) to the first filtered signal. The second filtering operation may at least partially remove the distortion introduced by the first filtering operation.

In some embodiments, the second transfer function is substantially the inverse of the first transfer function. The second transfer function may be offset from the inverse of the first transfer function in order to ensure the stability of the second filter. For example, at least one pole of the second transfer function may be adjusted or offset. In some embodiments, the first filter comprises an analog high pass filter and the second filter comprises a digital inverse high pass filter.

In some embodiments, a light source may be used to generate a photonic signal including at least one wavelength of light. The desired component of the detected light signal may correspond to the photonic signal. The light source may be driven by a light drive signal that includes a drive cycle that is repeated. In some embodiments, the drive cycle may include alternating periods during which light is emitted and no light is emitted by the light source. In some embodiments, when the light source is used to generate a photonic signal of two or more wavelengths of light, any suitable type of multiplexing may be used for the wavelengths of light such as time-division multiplexing, frequency-division multiplexing, CDMA multiplexing, any other suitable type of multiplexing, or any combination thereof.

In some embodiments, the processed physiological signal (e.g., the second filtered signal) may be used to determine one or more physiological parameters of the subject such as pulse rate, respiration rate, and blood oxygen saturation.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

The present disclosure is directed to processing physiological signals received from one or more sensors coupled to a subject. The physiological signals may be used by a physiological monitor to determine one or more physiological parameters of the subject. The sensors may include a light source for emitting light which may pass through perfused tissue of the subject. After the light has passed through the tissue of the subject it may be received by a detector. The detector may provide a signal proportional to the intensity of the received light. In some embodiments, the physiological signal provided by the detector may be representative of physiological information about the blood of the subject since light of different wavelengths passing through tissue may be differentially absorbed depending on, for example, oxygen saturation of the blood. The physiological monitor may analyze the physiological signal to determine one or more physiological parameters such as pulse rate, respiration rate, and oxygen saturation.

The physiological signal, however, may include one or more noise components. The noise components may include the effects of ambient light reaching the detector. Other sources of noise may include 50 or 60 Hz power line noise, subject movement, and/or other non-physiological or undesired physiological signal components. In some circumstances, the noise component can degrade the physiological signal being processed and decrease its signal-to-noise ratio. A low signal-to-noise ratio may make an accurate determination of the physiological parameter difficult.

Accordingly, the physiological signal being analyzed may be processed in order to reduce or remove the noise component. Additionally, the processing to reduce or remove the noise component may introduce unwanted distortion into the physiological signal. Therefore, the physiological signal may be further processed to reduce or remove the introduced distortion.

Figure 1:
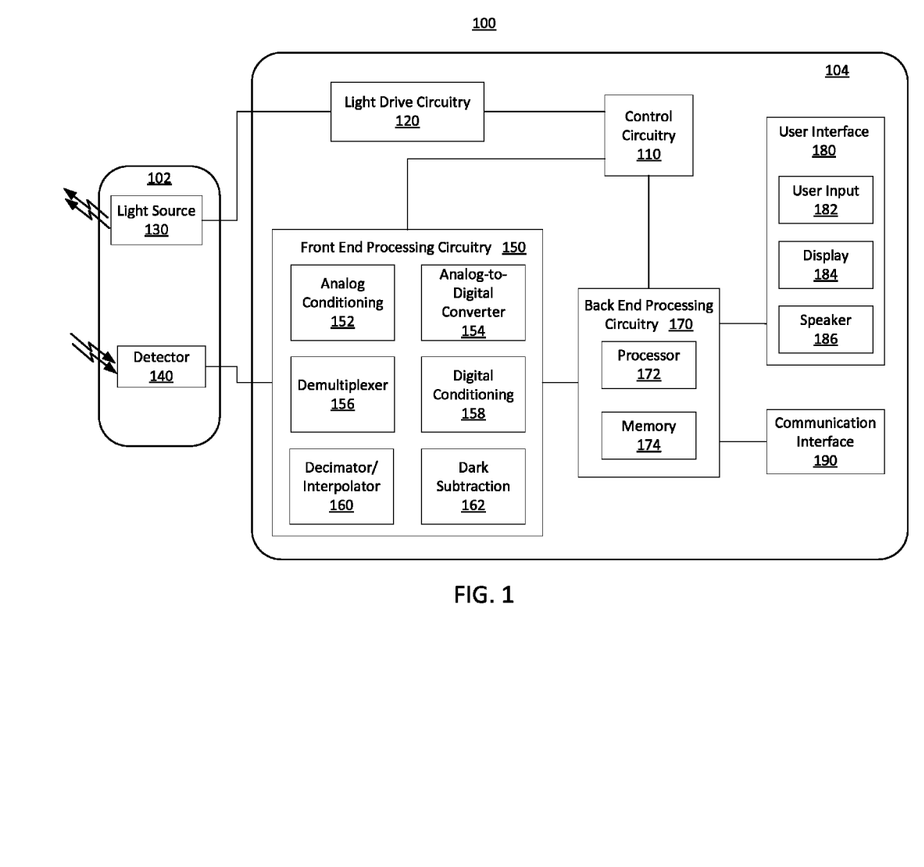
FIG. 1 is a block diagram of an illustrative physiological monitoring system in accordance with some embodiments of the present disclosure.

FIG. 1 is a block diagram of an illustrative physiological monitoring system 100 in accordance with some embodiments of the present disclosure. System 100 may include a sensor 102 and a monitor 104 for generating and processing physiological signals of a subject. In some embodiments sensor 102 and monitor 104 may be part of an oximeter.

Sensor 102 of physiological monitoring system 100 may include light source 130 and detector 140. Light source 130 may be configured to emit photonic signals having one or more wavelengths of light (e.g. Red and IR) into a subject's tissue. For example, light source 130 may include a Red light emitting light source and an IR light emitting light source, e.g. Red and IR light emitting diodes (LEDs), for emitting light into the tissue of a subject to generate physiological signals. In one embodiment, the Red wavelength may be between about 600 nm and about 700 nm, and the IR wavelength may be between about 800 nm and about 1000 nm. In embodiments where an array of sensors is used in place of single sensor 102, each sensor may be configured to emit a single wavelength. For example, a first sensor may emit only a Red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 140 may be chosen to be specifically sensitive to the chosen targeted energy spectrum of light source 130.

In some embodiments, detector 140 may be configured to detect the intensity of light at the Red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 140. After converting the received light to an electrical signal, detector 140 may send the detection signal to monitor 104, where the detection signal may be processed and physiological parameters may be determined (e.g., based on the absorption of the Red and IR wavelengths in the subject's tissue). In some embodiments, the detection signal may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate a light drive signal, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 110, as discussed above, may be configured to generate a light drive signal that is provided to light source 130 of sensor 102. The light drive signal may, for example, control the intensity of light source 130 and the timing of when light source 130 is turned on and off. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

Figure 2A:
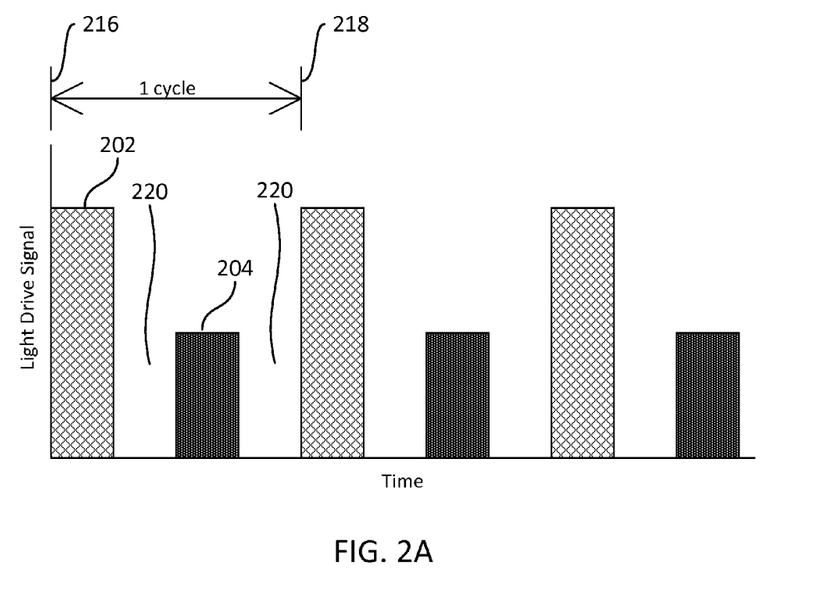
FIG. 2A shows an illustrative plot of a light drive signal in accordance with some embodiments of the present disclosure.

FIG. 2A shows an illustrative plot of a light drive signal comprising Red light drive pulse 202 and IR light drive pulse 204 in accordance with some embodiments of the present disclosure. Light drive pulses 202 and 204 may be generated by light drive circuitry 120 under the control of control circuitry 110. The light drive signal may be provided to light source 130 and Red light drive pulse 202 and IR light drive pulse 204 may be used to drive Red and IR light emitters, respectively, within light source 130. Red light drive pulse 202 may have a different amplitude than IR light drive pulse 204 since Red and IR light have different absorption in tissue depending on oxygenation levels. Additionally, the LEDs may have different efficiencies in converting current to light and the photodetector transfer function of light to electrical current may also depend on the wavelength of light. When the Red and IR light sources are driven in this manner they emit pulses of light at their respective wavelengths into the tissue of a subject in order generate physiological signals that physiological monitoring system 100 may process to calculate physiological parameters.

The light drive signal of FIG. 2A may also include dark periods 220 between the Red and IR light drive pulses. Dark periods 220 are periods during which no drive current may be applied to light source 130. Dark periods 220 may be provided, for example, to prevent overlap of the emitted light, since light source 130 may require time to turn completely on and completely off. The period from time 216 to time 218 may be referred to as a drive cycle, which includes four segments: a Red light drive pulse 202, followed by a dark period 220, followed by an IR light drive pulse 204, and followed by a dark period 220. After time 218 the drive cycle may be repeated (e.g., as long as a light drive signal is provided to light source 130). It will be understood that the starting point of the drive cycle is merely illustrative and that the drive cycle can start at any location within FIG. 2A, provided the cycle spans two light drive pulses and two dark periods. Thus, each Red light drive pulse 202 and each IR light drive pulse 204 may be understood to be surrounded by two dark periods 220.

It will be understood that the light drive signal shown in FIG. 2A is merely illustrative and that any other suitable light drive schemes may be used. For example, in some embodiments, the drive cycle my include three segments instead of four, where one of the dark periods shown in FIG. 2A is eliminated. As another example, while FIG. 2A illustrates a time-division multiplexing scheme for the Red and IR light emitters, other multiplexing schemes may be used such as frequency division multiplexing (e.g., where the emitters are modulated at different frequencies), CDMA multiplexing, any other suitable type of multiplexing, or any combination thereof.

Referring back to FIG. 1, front end processing circuitry 150 may receive a detection signal from detector 140 and provide one or more processed signals to back end processing circuitry 170. The term "detection signal," as used herein, may refer to any of the signals generated within front end processing circuitry 150 as it processes the output signal of detector 140. Front end processing circuitry 150 may perform various analog and digital processing of the detector signal. One suitable detector signal that may be received by front end processing circuitry 150 is shown in FIG. 2B.

Figure 2B:
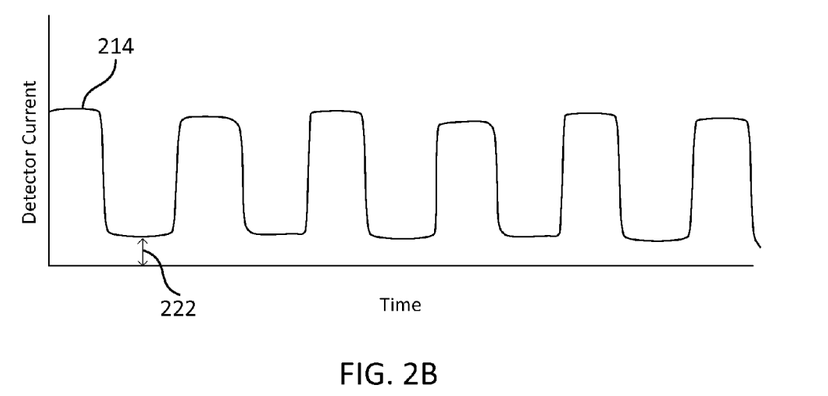
FIG. 2B shows an illustrative plot of a detector signal in accordance with some embodiments of the present disclosure.

FIG. 2B shows an illustrative plot of detector signal 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with light drive pulses driving one or more emitters of a light source, such as light source 130 of FIG. 1. For example, detector current waveform 214 may be generated in response to a light source being driven by the light drive signal of FIG. 2A. The valleys of detector current waveform 214 may be synchronous with periods of time during which no light is being emitted by the light source. While no light is being emitted by a light source during the valleys, detector current waveform 214 may not fall all of the way to zero. Rather, dark current 222 may be present in the detector waveform. Since dark current 222 may interfere with accurate determinations of physiological characteristics, dark current 222 may be removed as discussed in more detail below.

It will be understood that the detector signal shown in FIG. 2B is merely illustrative. In some embodiments, it may be desirable to generate Red and IR peaks in the detector signal that are of similar amplitude (e.g., as shown in FIG. 2B). In some embodiments, it may not be desirable or possible to generate Red and IR peaks in the detector signal that are of similar amplitude. For example, it may be difficult to generate a sufficiently sized Red peak for subjects with dark pigment or with thick fingers. In such a situation, the IR peaks in the detectors signal may be generated with a larger amplitude to facilitate, for example, a heart rate calculation even if it may be difficult to calculate oxygen saturation.

Referring back to FIG. 1, front end processing circuitry 150, which may receive a detection signal, such as detector current waveform 214, may include analog conditioning 152, analog-to-digital converter 154, demultiplexer 156, digital conditioning 158, decimation/interpolator 160, and dark subtraction 162.

Analog conditioning 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signal may be processed by analog-to-digital converter 154, which may convert the conditioned analog signal into a digital signal. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a Red component, an IR component, and at least one dark component. Demultiplexer 156 may operate on detector current waveform 214 of FIG. 2B to generate a Red signal, an IR signal, a first dark signal (e.g., corresponding to the dark component that occurs immediately after the Red component), and a second dark signal (e.g., corresponding to the dark component that occurs immediately after the IR component). Demultiplexer 156 may operate under the control of control circuitry 110. For example, demultiplexer 156 may use timing control signals from control circuitry 110 to identify and separate out the different components of the detector signal. In some embodiments, demultiplexer 156 may perform demodulation operations in addition to or in place of demultiplexing operations.

Digital conditioning 158 may perform any suitable digital conditioning of the detector signal. The digital conditioning may include any type of digital filtering of the signal (e.g., low pass, high pass, band pass, notch, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Dark subtraction 162 may be performed on the digital signal. In some embodiments, dark subtraction 162 may subtract dark values from the Red and IR components to generate adjusted Red and IR signals.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signal by analog conditioning 152 to map the expected range of the detection signal to the full or close to full output range of analog-to-digital converter 154. The output value of analog-to-digital converter 154, as a function of the total analog gain applied to the detection signal, may be given as:

$$\text{ADC Value} \propto \text{Total Analog Gain} \times [\text{Ambient Light} + \text{LED Light}].$$

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signal, thereby increasing the resolution of the converted signal. In some embodiments, the total analog gain may be reduced by a small amount so that small changes in the light level incident on the detector do not cause saturation of analog-to-digital converter 154.

However, if the contribution of ambient light is large relative to the contribution of light from a light source, the total analog gain applied to the detection current may need to be reduced to avoid saturating analog-to-digital converter 154. When the analog gain is reduced, the portion of the signal corresponding to the light source may map to a smaller number of analog-to-digital conversion bits. Thus, more ambient light noise in the input of analog-to-digital converter 154 may results in fewer bits of resolution for the portion of the signal from the light source. This may have a detrimental effect on the signal-to-noise ratio of the detection signal. Therefore, it may be desirable to reduce the effect of ambient light on the detection signal that is applied to analog-to-digital converter 158, and thereby reduce the contribution of the noise component to the converted digital signal.

Back end processing circuitry 170 may include processor 172 and memory 174. Processor 172 may be adapted to execute software, which may include an operating system and one or more applications, as part of performing the functions described herein. Processor 172 may receive and further physiological signals received from front end processing circuitry 150. For example, processor 172 may determine one or more physiological parameters based on the received physiological signals. Memory 174 may include any suitable computer-readable media capable of storing information that can be interpreted by processor 172. This information may be data or may take the form of computer-executable instructions, such as software applications, that cause the microprocessor to perform certain functions and/or computer-implemented methods, Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with use interface 180 and communication interface 190.

User interface 180 may include user input 182, display 184, and speaker 186. User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth. In an embodiment, the subject may be a medical patient and display 184 may exhibit a list of values which may generally apply to the patient, such as, for example, age ranges or medication families, which the user may select using user inputs 182. Additionally, display 184 may display, for example, an estimate of a subject's blood oxygen saturation generated by monitor 104 (referred to as an "SpO$_2$" measurement), pulse rate information, respiration rate information, blood pressure, any other parameters, and any combination thereof Display 184 may include any type of display such as a cathode ray tube display, a flat panel display such a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, communications buses, communications protocols, device identification protocols, any other suitable hardware or software, or any combination thereof. Communications interface 190 may be configured to allow wired communication (e.g., using USB, RS-232 or other standards), wireless communication (e.g., using WiFi, IR, WiMax, BLUETOOTH, UWB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In other embodiments, the functionality of one or more of the components may be performed in a different order or may not be required. In an embodiment, all of the components of physiological monitoring system 100 can be realized in processor circuitry.

Figure 3:
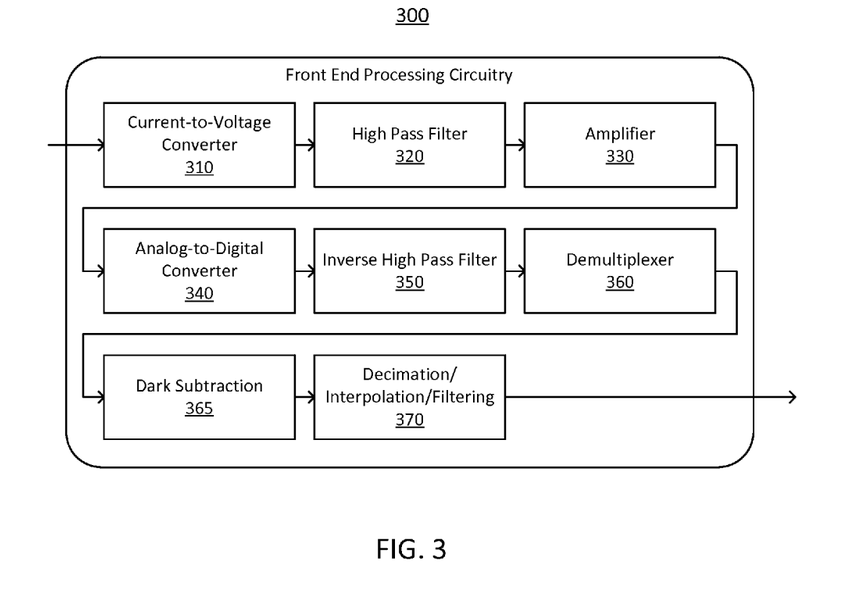
FIG. 3 shows a block diagram of illustrative front end circuitry in accordance with some embodiments of the present disclosure.

FIG. 3 shows a block diagram of illustrative front end processing circuitry 300 in accordance with some embodiments of the present disclosure for receiving and processing signals from a sensor device. In some embodiments, front end processing circuitry 300 may be included in a physiological monitoring system such as system 100 of FIG. 1. In such embodiments, front end processing circuitry 300 may receive and process signals from sensor 102 of FIG. 1. Front end processor circuitry 300 may include current-to-voltage converter 310 which may convert a current signal into a voltage signal. For example, current-to-voltage converter 310 may receive and convert a detector current waveform such as detector current waveform 214 of FIG. 2B. Front end processing circuitry 300 may also include high pass filter 320 which may filter the detection signal. Amplifier 330 and analog-to-digital converter 340 may also be included in front end processing circuitry 300. The detection signal in front end processing circuitry 300 may also be filtered by inverse high pass filter 350 and demultiplexed by demultiplexer 360. Dark subtraction 365 and decimation/interpolation/filtering 370 may also be included within front end processing circuitry 300.

In an embodiment, the components of front end processing circuitry 300 that are shown and described may be implemented in a single processor system. In other embodiments the functionality of some of the components may be implemented in separate components. For example, the functionality of some or all of the components may be implemented in back end processing circuitry or in other processor circuitry. In other embodiments, the functionality of one or more of the components may not be required. In some embodiments, components 310, 320, and 330 may all be analog conditioning components that may be in implemented as part of analog conditioning 152 of FIG. 1. In some embodiments, components 340, 360, and 365 may be implemented as part of analog-to-digital converter 154, demultiplexer 156, and dark subtraction 162 of FIG. 1, respectively, and include the functionality of these components as described above. In some embodiments, decimation/interpolation/filtering 370 may be implemented as part of digital conditioning 158 and decimator/interpolator 160 of FIG. 1 and include the functionality of these components as described above. In some embodiments, inverse high pass filter 350 may be implemented as part of digital conditioning 158 of FIG. 1. In some embodiments, an anti-aliasing filter (e.g., a low pass filter) may be included in front end processing circuitry 300. The anti-aliasing filter may be included, for example, as part of amplifier 330 or between amplifier 330 and analog-to-digital converter 340

Front end processing circuitry 300 may receive a detection signal such as detector current waveform 214 of FIG. 2B when light from a light source is incident on a detector, which converts the intensity of the received light into an electrical detection signal. The amplitude of the detection signal may be proportional to the light incident upon the detector. Since the detection signal from the detector may be a small current signal, it may be converted to a voltage signal and amplified before being converted to a digital signal. Accordingly, in some embodiments, current-to-voltage converter 310 may receive the detection signal from the detector and convert the detection signal from a current detection signal to a voltage detection signal. The resulting detection signal may be filtered by high pass filter 320.

High pass filter 320 may provide a method for removing or attenuating a substantial amount of noise from the detection signal, including the effect of ambient light on the detection signal. Ambient light incident on the detector such as detector 140 of FIG. 1 may be at a relatively low frequency. The light source, such as light source 130 of FIG. 1, may be modulated at a relatively high frequency. For example, the repetition rate for the drive cycle, such as the drive cycle shown in FIG. 2A, may be 625 Hz, 1211 Hz, 311 Hz, or any other suitable frequency. Therefore, it may be possible for high pass filter 320 to substantially pass the peaks of the detection signal such as detector current waveform 214 of FIG. 2B while stripping away or substantially attenuating the ambient light or dark component before it reaches the analog-to-digital converter. Depending on the cutoff frequency of high pass filter 320, high pass filter 320 may also reject other noise in the detection signal such as the lower harmonics of AC line noise or fluorescent lighting. Additionally, high pass filter 320 may substantially attenuate any other low frequency components which may be present in the detection signal, including any DC levels which may be present at the emitters of the light source during periods when the LEDs are turned on.

The detection signal filtered by high pass filter 320 may then be amplified by amplifier 330 prior to conversion to a digital signal by analog-to-digital converter 340. The use of high pass filter 320 may allow front end processing circuitry 300 to apply more analog gain to the detection signal, thereby providing a better signal-to-noise ratio.

The filtering by high pass filter 320, however, may introduce unwanted distortion into the high pass filtered detection signal. For example, the filter may attenuate all low frequency components including the DC levels during the light source on times and the dark periods when rectangular pulses are used to modulate the light source. This may cause overshoot or droop in the different detection signal segments. Using a duty cycle of 50% will cause high pass filter 320 to be centered. Because of the distortion that may be introduced by high pass filter 320, the detection signal may be further filtered by inverse high pass filter 350. Filtering of the detection signal by inverse high pass filter 350 may remove the distortion in the detection signal that was introduced by high pass filter 320. One important benefit of the inverse high pass filter is that by removing the unwanted distortions, the signal levels of the dark periods are equalized. The equalization of the dark periods may be achieved when the Red and IR peaks in the detection signal are of similar and different amplitudes. The detection signal may then be demultiplexed by demultiplexer 360. It will be understood that demultiplexing of the detection signal can be performed in the analog domain or the digital domain.

Dark subtraction may then be performed on the detection signal by dark subtraction 365. It will be understood that dark subtraction may be performed on the detection signal after high pass filtering of the detection signal, since some non-zero dark signal may still remain after the filtering. In dark subtraction 365, a subtraction amount is determined from the dark signal portion of the detection signal and subtracted from the peak portion of the detection signal in order to reduce the effect of dark signal on the peak. For example, in reference to FIG. 2A, a detection signal peak corresponding to Red light drive pulse 202 may be adjusted by determining the amount of dark signal during the dark period 220 preceding Red light drive pulse 202. The dark signal amount determined in this manner may be subtracted from the detector peak corresponding to Red light drive pulse 202. Alternatively, the dark period 220 after Red light drive pulse 202 may be used to correct Red light drive pulse 202 rather than the dark period 220 preceding it. Additionally, an average of the dark periods 220 before and after Red light drive pulse 202 may be used. It will be understood that the dark subtraction need not be performed on the detection signal immediately after demultiplexing, and that it may be performed at any other suitable point within front end processing circuitry 300.

Figure 4:
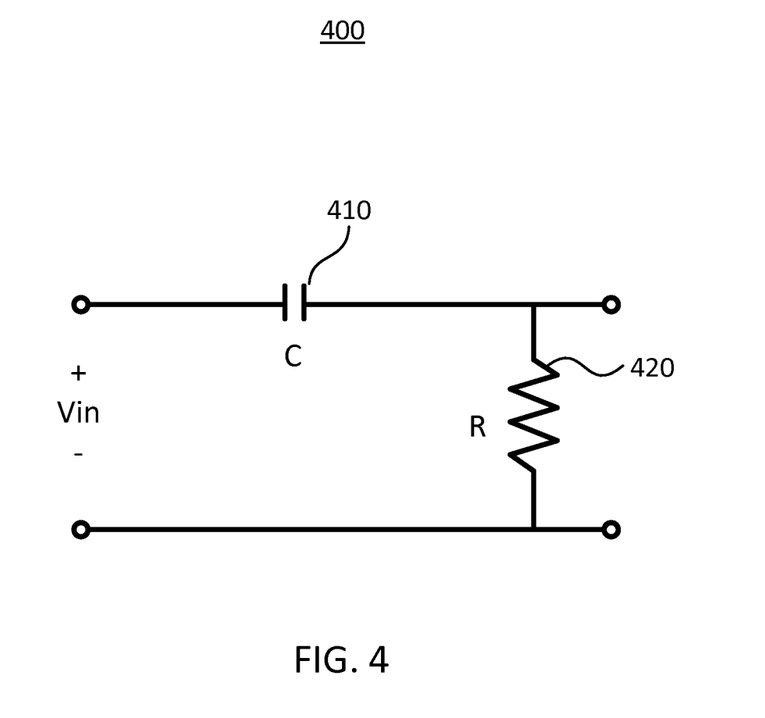
FIG. 4 is a schematic representation of an illustrative filter in accordance with some embodiments of the present disclosure.

FIG. 4 is a schematic representation of an illustrative high pass filter 400 in accordance with some embodiments of the present disclosure. In some embodiments high pass filter 400 may perform the function of a high pass filter such as high pass filter 320 of front end processing circuitry 300 of FIG. 3 High pass filter 400 may include capacitor 410 and resistor 420. Although any type of high pass filter may be used within front end processing circuitry 300, single pole high pass filter 400, may provide a passive technique for performing the functions of high pass filter 320 simply and inexpensively.

High pass filter 400 has the following transfer function:

$$H(s) = \frac{Vout}{Vin} = \frac{iR}{i\left(R + \frac{1}{sC}\right)} = \frac{sRC}{sRC+1} \qquad (1)$$

The cutoff frequency of this filter may be at $s=1/(RC)$ radians per second, or $f_c=1/(2\pi RC)$ Hz. In the s domain, high pass filter 400 has a zero at 0 and a pole at $s=-1/(RC)$. Since this pole may be in the left hand plane for all positive (realizable) values of capacitor 410 and resistor 420, the stability of high pass filter 400 may be guaranteed.

High pass filter 400 can also be implemented as a digital filter. Using the reciprocal of the sample rate of the analog-to-digital converter (in Hz) as the sample interval, T, an equivalent digital filter may be estimated by applying the bilinear transform by substituting for s as shown below.

$$s = \frac{2(z-1)}{T(z+1)} = \frac{2(1-z^{-1})}{T(1+z^{-1})} \qquad (2)$$

$$H(z) = \frac{\frac{2RC(1-z^{-1})}{T(1+z^{-1})}}{\frac{2RC(1-z^{-1})}{T(1+z^{-1})}+1} \qquad (3)$$

$$= \frac{1-z^{-1}}{(1-z^{-1})+\frac{T(1+z^{-1})}{2RC}}$$

$$= \frac{1-z^{-1}}{\left(\frac{T}{2RC}+1\right)+\left(\frac{T}{2RC}-1\right)z^{-1}}$$

The transfer function may be that of an infinite impulse response filter with the following form:

$$H(z) = \frac{B(z)}{A(z)} = \frac{b_0 + b_1 z^{-1}}{a_0 + a_1 z^{-1}} = \frac{1-z^{-1}}{\left(\frac{T}{2RC}+1\right)+\left(\frac{T}{2RC}-1\right)z^{-1}}. \qquad (4)$$

From the transfer function above, b=[1 −1] and $$a = \left[\left(\frac{T}{2RC}+1\right)\left(\frac{T}{2RC}-1\right)\right].$$

Forming high pass filter 400 as a part of a differential circuit may add a gain of 2, and may not affect the frequency response after gain is normalized to 0 dB. High pass filter 400 can be rescaled to the standard form where $a_0=1.0$ by dividing each coefficient by $a_0$.

High pass filter 400 may have a zero located on the unit circle at a complex value of 1+0i. The complex pole may be determined starting with the following equation:

$$\left(\frac{T}{2RC}+1\right)+\left(\frac{T}{2RC}-1\right)z^{-1} = 0. \qquad (5)$$

Equation (5) can be rearranged to solve for z as follows:

$$z^{-1} = \frac{-\left(\frac{T}{2RC}+1\right)}{\left(\frac{T}{2RC}-1\right)} = \frac{-(T+2RC)}{(T-2RC)} = \frac{-(T+2RC)}{(T-2RC)} \qquad (6)$$

$$z = \frac{2RC-T}{2RC+T}.$$

In the following equation, the numerator of the pole may be less than the denominator, since R, C, and T may all be guaranteed to be positive in physically realizable systems. This may guarantee stability with the pole positioned inside the unit circle. The pole of high pass filter 400 can be expressed as follows.

$$\text{pole} = \frac{2RC-T}{2RC+T} + 0i \qquad (7)$$

Figure 5A:
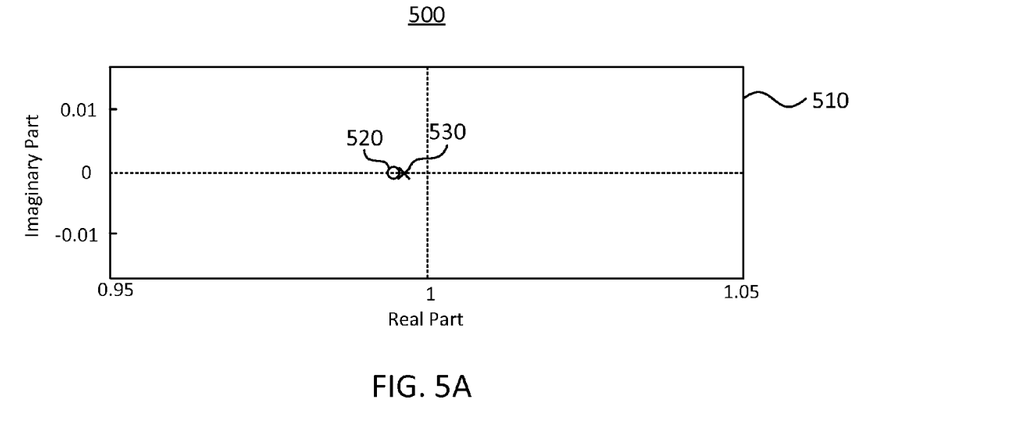
FIGS. 5A and 5B show illustrative pole-zero plots of inverse high pass filters in accordance with some embodiments of the present disclosure.
Figure 5B:
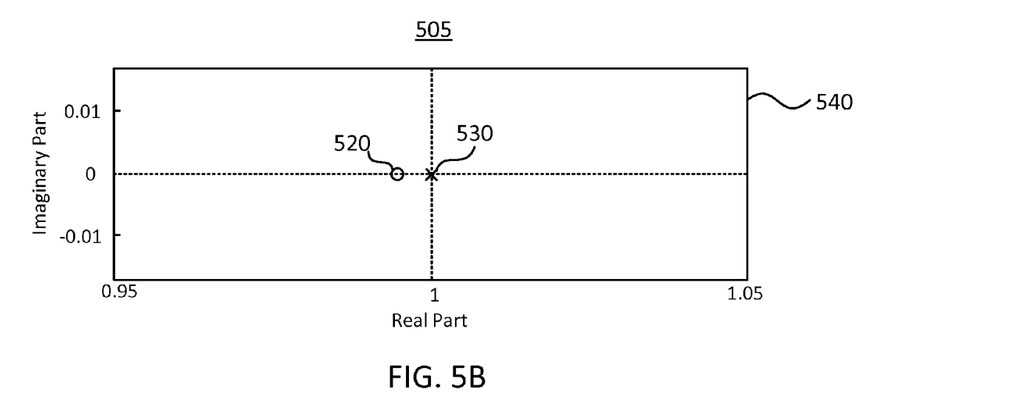

FIGS. 5A and 5B show illustrative pole-zero plots 510 and 540 of inverse high pass filters in accordance with an embodiment of the present disclosure. In some embodiments, plots 510 and 540 may correspond to inverse high pass filters that may be implemented in inverse high pass filter 350 of FIG. 3. In order for an inverse high pass filter to be stable, its pole may be contained within the unit circle. The inverse high pass filter of the present disclosure may have a transfer function that is the reciprocal of the transfer function of the high pass filter, i.e. the reciprocal of H(z). As illustrated, plots 510 and 540 correspond to the reciprocal of the transfer function of high pass filter 400 of FIG. 4. The poles and zeros of high pass filter 400 may be swapped to obtain the transfer function of the inverse high pass filter. For the inverse high pass filter to be stable, the zero of high pass filter 400 may be contained within the unit circle. However, a zero of high pass filter 400 may be located on the unit circle. Therefore, a stable version of the inverse high pass filter may be approximated. In an embodiment this may be accomplished by adding a small constant α to the denominator of the transfer function of inverse high pass filter 350 as shown below. In this manner the poles of $\alpha_{inv}$ may be stabilized.

$$b_{inv} = a \quad a_{inv} = b + \alpha \qquad (8)$$

The addition of α in this manner may cause the response of the inverse high pass filter to deviate slightly from an ideal filter response. However, it may stabilize the inverse high pass filter.

The computational requirements of the inverse high pass filter may be reasonably low. The requirements may be similar to the computational requirements of applying a first order infinite impulse filter to a single waveform at the sample rate of the analog-to-digital converter.

In an embodiment, capacitor 410 may have a value of 0.1 μF and resistor 420 may have a value of 51 kΩ for high pass filter 400 of FIG. 4. If a sample rate of 25 kHz is used (i.e., T=40 μS), the value of α=0.002 may be used to stabilize the poles of $a_{inv}$. In practice, the RC time constant of the inverse high pass filter may need to be adjusted to compensate for the effects of α or the effect of other components in the circuit. The RC time constant can be provided with a predetermined adjustment, or it can be adjusted dynamically to maintain a flat response to square wave inputs or dark periods 220. If the RC time constant is too large the square wave response may show droop. If the RC time constant is too small the square wave response may deflect upwards.

Pole-zero plot 540 is a complex plane showing pole 530 and zero 520 of the inverse high pass filter before adding the constant α to the denominator of the transfer function of the inverse high pass filter. Pole 530 is located on the unit circle of the complex plane. However, if a pole of a filter is not within the unit circle of a complex plane the filter may not be stable. Since the pole 530 of the inverse high pass filter 350 is on the unit circle, the constant α may be added to move pole 530 inside the unit circle. Pole-zero plot 510 shows pole 530 and zero 520 of inverse high pass filter 350 after the addition of the constant α. The addition of the constant α has caused pole 530 to be located inside the unit circle of pole-zero plot 510. Thus, the inverse high pass filter may be stabilized using the constant α. In some embodiments, the high pass filter may be realized in analog hardware and inverse high pass filter may be realized in software.

Figure 6:
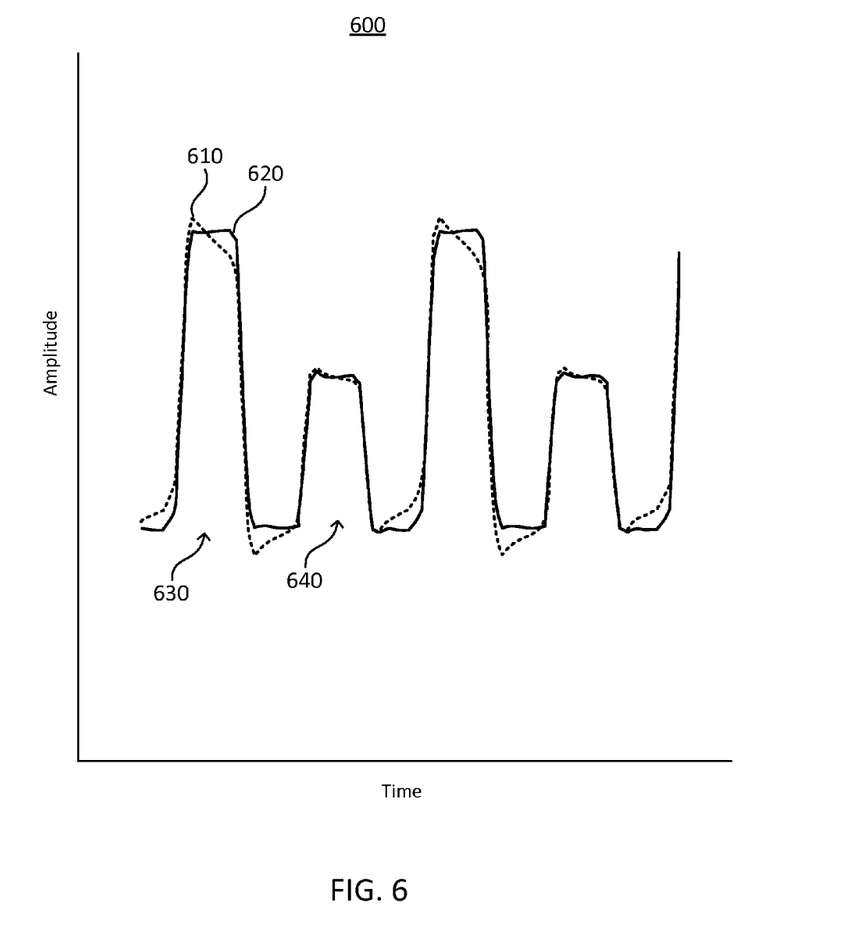
FIG. 6 shows an illustrative plot of detection signals that may be produced within front end processing circuitry in accordance with some embodiments of the present disclosure.

FIG. 6 shows an illustrative plot 600 of detection signals that may be produced within front end processing circuitry such as front end circuitry 150 of FIG. 1 or front end circuitry 300 of FIG. 3, in accordance with some embodiments of the present disclosure. The signals represented on plot 600 include ADC signal 610, represented by a dotted curve, that may appear at the output of an analog-to-digital converter, before it is applied to an inverse high pass filter. ADC signal 610 may have been filtered by a high pass filter such as high pass filter 400 of FIG. 4 prior to conversion to a digital signal by the analog-to-digital converter. Thus, noise such as the noise due to ambient light may have been significantly removed from ADC signal 610. Plot 600 also includes inverse filtered signal 620, represented as a solid curve, that may appear at the output of an inverse high pass filter such as inverse high pass filter 350 of FIG. 3. For example, inverse high pass filter 350 may receive ADC signal 610, filter it, and thereby provide as an output inverse filtered signal 620.

ADC signal 610 and inverse filtered signal 620 may be generated when light drive signals such as the light drive signal shown in FIG. 2A are applied to a light source causing light to be emitted and received by a detector. For example, in some embodiments, Red waveform peak 630 may occur in response to Red light drive pulse 202 of FIG. 2A, and IR waveform peak 640 may occur in response to IR light drive pulse 204 of FIG. 2A. Furthermore, the valleys of ADC signal 610 and inverse filtered signal 620 may correspond to dark periods 220 of FIG. 2A between Red light drive pulses and IR light drive pulses, when no light is emitted from a light source. ADC signal 610 and inverse filtered signal 620 are shown with a 50% duty cycle. The amplitudes of the red and IR waveform peaks are shown with different amplitudes for purposes of illustration. It will be understood that the amplitudes may be similar or different.

The shape of ADC signal 610 during Red waveform peak 630 includes an overshoot as it rises, and a droop before it reaches its falling edge. Additionally, ADC signal 610 includes an overshoot at the bottom of the falling edge of Red waveform peak 630 and drifts upwards during the dark period after Red waveform peak 630. Furthermore, during the dark period after IR waveform peak 640, ADC signal 610 begins drifting upwards before the rising edge of the next Red waveform peak. These features of ADC signal 610 may be distortion introduced into the detection signal when it is filtered by a high pass filter such as high pass filter 400 of FIG. 4.

As previously described, the poles and zeros of high pass filter 400 may be swapped in order to provide an inverse high pass filter. Therefore, the inverse high pass filter may be effective to undo the unwanted effects of high pass filter 400 and remove the foregoing distortion from ADC signal 610. Inverse filtered signal 620 may represent the result of applying ADC signal 610 to an inverse high pass filter, in order to remove the foregoing distortion. For example, during Red waveform peak 630 inverse filtered signal 620 does not have the overshoot or downward droop of ADC signal 610.

Furthermore, inverse filtered signal 620 does include the overshoot at the bottom of the falling edge of Red waveform peak 630 or drift upwards during the dark period after Red waveform peak 630. Additionally, inverse filtered signal 620 does not drift upwards during the dark period after IR waveform peak 640. Accordingly, the inverse high pass filter may be effective to remove the distortion created in the detection signal by high pass filter 400 when high pass filter 400 removes the noise, such as ambient light. Additionally, applying the inverse high pass filter may help flatten the amplitudes of the dark periods and bring them to the same or similar level. Equalizing the dark periods and making them more consistent may assist in accurately determining the physiological parameters from the inverse high pass filtered signals.

In view of the foregoing, the present disclosure provides techniques for processing a physiological signal such as a detection signal. The detection signal may be received from a detector and include noise such as ambient light noise. The detection signal may be conditioned to reduce or attenuate the noise. Distortions, which may be introduced by the conditioning, may be removed. This may include equalizing and flattening the dark periods of the signal and flattening the tops of light pulse periods of the signal. Physiological parameters may then be accurately calculated based upon the processed detection signal The physiological parameters that can be calculated may include, for example, pulse rate, respiration rate, blood oxygen saturation, blood pressure, any other suitable parameters, or any combination thereof. These physiological parameters can be calculated using any known calculation techniques. It will be understood that while a high pass fitter and an inverse high pass filter were disclosed for processing the physiological signals, any other suitable filters and inverse filters may be used for removing noise and removing distortions introduced by the filtering.

Figure 7:
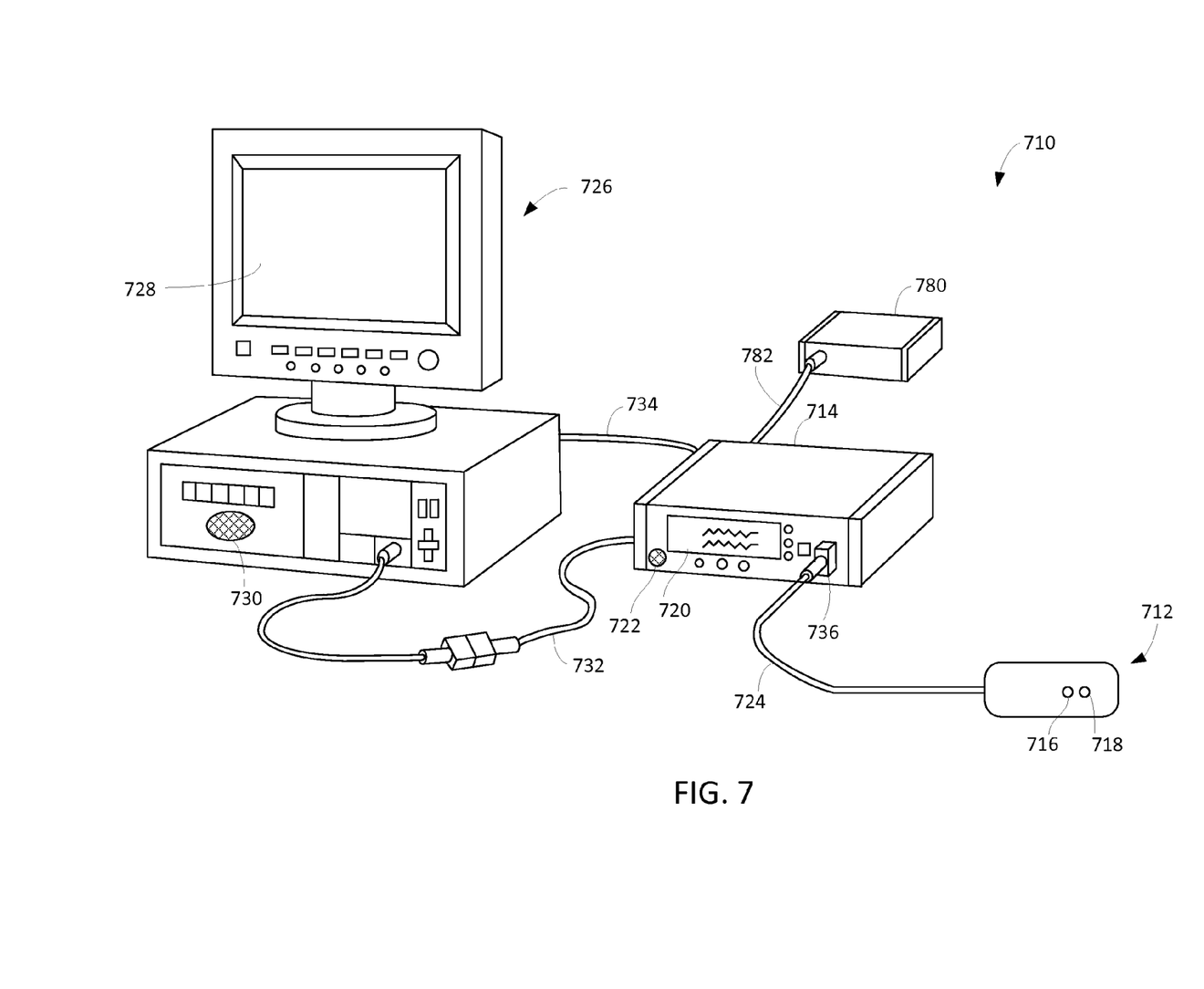
FIG. 7 shows an illustrative physiological monitoring system in accordance with some embodiments of the present disclosure.

FIG. 7 is a perspective view of an embodiment of physiological monitoring system 710. In some embodiments, one or more components of physiological monitoring system 710 may include the front end processing of the present disclosure. For example, physiological monitoring system 710 may include front end processing circuitry 300 of FIG. 3 or one or more components of physiological monitoring system 100 of FIG. 1.

Physiological monitoring system 710 may include a monitor 714 which may be coupled to sensor unit 712. In some embodiments, sensor unit 712 may be part of an oximeter. Additionally, monitor 714 may be wirelessly coupled (not shown) to sensor unit 712. Sensor unit 712 may include light source 716 for emitting light at one or more wavelengths into a subject's tissue. Detector 718 may also be provided in sensor unit 712 for detecting the light originally from light source 716 that emanates from the subject's tissue after passing through the tissue. Any suitable physical configuration of light source 716 and detector 718 may be used. In an embodiment, sensor unit 712 may include multiple emitters and/or detectors, which may be spaced apart. Physiological monitoring system 710 may also include one or more additional sensor units (not shown) which may take the form of any of the embodiments described herein with reference to sensor 102 or sensor unit 712. An additional sensor unit may be the same type of sensor unit as sensor unit 712, or a different sensor unit type than sensor unit 712.

Calibration device 780, which may be powered by monitor 714, a battery, or by a conventional power source such as a wall outlet, may include any suitable calibration device. Calibration device 780 may be communicatively coupled to monitor 714 via communicative coupling 782, and/or may communicate wirelessly (not shown). In some embodiments, calibration device 780 is completely integrated within monitor 714. In some embodiments, calibration device 780 may include a manual input device (not shown) used by an operator to manually input reference signal measurements obtained from some other source (e.g., an external invasive or non-invasive physiological measurement system).

Multiple sensor units may be capable of being positioned at two different locations on a subject's body; for example, a first sensor unit may be positioned on a subject's forehead, while a second sensor unit may be positioned at a subject's fingertip. Sensor units may each detect any signal that carries information about a subject's physiological state, such as arterial line measurements or the pulsatile force exerted on the walls of an artery using, for example, oscillometric methods with a piezoelectric transducer. According to another embodiment, system 710 may include a plurality of sensors forming a sensor array in lieu of either or both of the sensor units. Each of the sensors of a sensor array may be a complementary metal oxide semiconductor (CMOS) sensor. Alternatively, each sensor of an array may be a charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, light source 716 and detector 718 may be on opposite sides of a digit such as a finger or toe, in which case the light that is emanating from the tissue has passed completely through the digit. In an embodiment, light source 716 and detector 718 may be arranged so that light from light source 716 penetrates the tissue and is reflected by the tissue into detector 718, such as in a sensor designed to obtain pulse oximetry data from a subject's forehead.

In some embodiments, a sensor may be connected to and draw its power from monitor 714. In another embodiment, a sensor wirelessly connected to monitor 714 may include its own battery or similar power supply (not shown). Monitor 714 may be configured to calculate physiological parameters (e.g., pulse rate, blood pressure, blood oxygen saturation) based at least in part on data relating to light emission and detection received from one or more sensor units such as sensor unit 712. In an alternative embodiment, the calculations may be performed on the sensor units or an intermediate device and the result of the calculations may be passed to monitor 714. Further, monitor 714 may include a display 720 configured to display the physiological parameters or other information about the system. In the embodiment shown, monitor 714 may also include a speaker 722 to provide an audible sound that may be used in various other embodiments, such as for example, sounding an audible alarm in the event that a subject's physiological parameters are not within a predefined normal range. In some embodiments, the monitor 714 includes a blood pressure monitor. In some embodiments, the system 710 includes a stand-alone blood pressure monitor in communication with the monitor 714 via a cable or a wireless network link. In an embodiment, a sensor such as sensor unit 712 may be communicatively coupled to monitor 714 via cable connection port 736. The cable connection may be used instead of or in addition to a wireless connection.

In the illustrated embodiment, system 710 includes a multi-parameter physiological monitor 726. The monitor 726 may include a cathode ray tube display, a flat panel display (as shown) such as a liquid crystal display (LCD) or a plasma display, or may include any other type of monitor now known or later developed. Multi-parameter physiological monitor 726 may be configured to calculate physiological parameters and to provide a display 728 for information from monitor 714 and from other medical monitoring devices or systems (not shown). For example, multi-parameter physiological monitor 726 may be configured to display pulse rate information from monitor 714, an estimate of a subject's blood oxygen saturation generated by monitor 714 (referred to as an "$SpO_2$" measurement), and blood pressure from monitor 714 on display 728. Multi-parameter physiological monitor 726 may include a speaker 730.

Monitor 714 may be communicatively coupled to multi-parameter physiological monitor 726 via a cable 732 or 734 or a digital communications port, respectively and/or may communicate wirelessly. In addition, monitor 714 and/or multi-parameter physiological monitor 726 may be coupled to a network to enable the sharing of information with servers or other workstations (not shown). Monitor 714 may be powered by a battery (not shown) or by a conventional power source such as a wall outlet.

Figure 8:
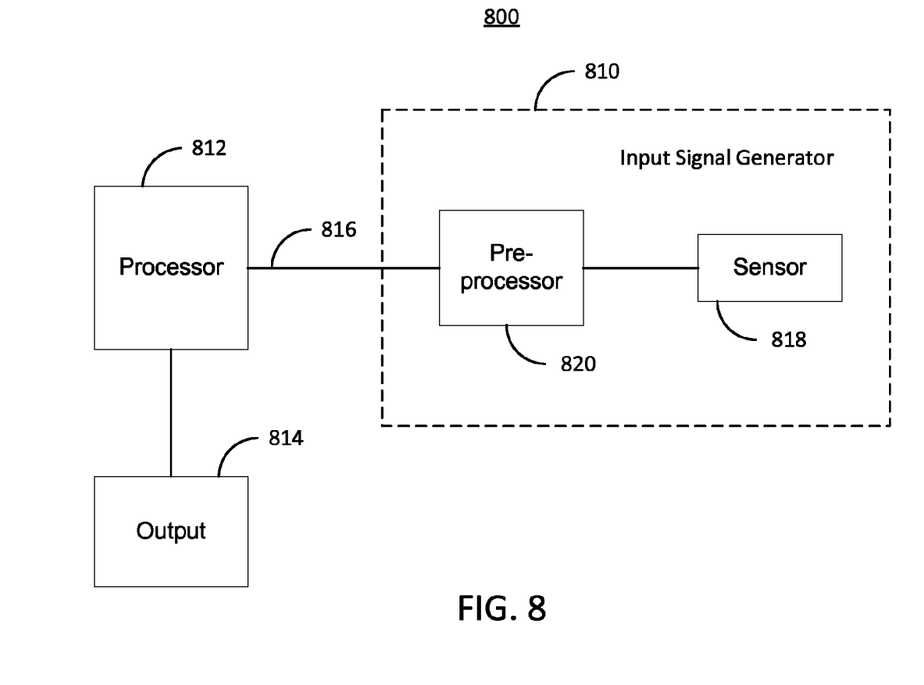
FIG. 8 shows a block diagram of an illustrative signal processing system in accordance with some embodiments of the present disclosure.

FIG. 8 is an illustrative signal processing system 800 in accordance with an embodiment that may implement the signal processing techniques described herein. Signal processing system 800 includes input signal generator 810, processor 812 and output 814. In the illustrated embodiment, input signal generator 810 may include pre-processor 820 coupled to sensor 818. As illustrated, input signal generator 810 generates an input signal 816. In some embodiments, input signal 816 may include one or more intensity signals based on a detector output. In some embodiments, pre-processor 820 may be an oximeter and input signal 816 may be a PPG signal. In an embodiment, pre-processor 820 may be any suitable signal processing device and input signal 816 may include PPG signals and one or more other physiological signals. It will be understood that input signal generator 810 may include any suitable signal source, signal generating data, signal generating equipment, or any combination thereof to produce signal 816. Signal 816 may be a single signal, or may be multiple signals transmitted over a single pathway or multiple pathways.

Pre-processor 820 may apply one or more signal processing operations to the signal generated by sensor 818. For example, pre-processor 820 may apply a pre-determined set of processing operations to the signal provided by sensor 818 to produce input signal 816 that can be appropriately interpreted by processor 812, such as performing A/D conversion. In some embodiments, A/D conversion may be performed by processor 812. Pre-processor 820 may also perform any of the following operations on the signal provided by sensor 818: reshaping the signal for transmission, multiplexing the signal, modulating the signal onto carrier signals, compressing the signal, encoding the signal, and filtering the signal. In some embodiments, pre-processor 820 may include a current-to-voltage converter (e.g., to convert a photocurrent into a voltage), an amplifier, a filter, and A/D converter, a de-multi-plexer, any other suitable pre-processing components, or any combination thereof. In some embodiments, pre-processor 820 may include one or more components from front end processing circuitry 300 of FIG. 3.

In some embodiments, signal 816 may include PPG signals corresponding to one or more light frequencies, such as an IR PPG signal and a Red PPG signal. In some embodiments, signal 816 may include signals measured at one or more sites on a subject's body, for example, a subject's finger, toe, ear, arm, or any other body site. In some embodiments, signal 816 may include multiple types of signals (e.g., one or more of an ECG signal, an EEG signal, an acoustic signal, an optical signal, a signal representing a blood pressure, and a signal representing a heart rate). Signal 816 may be any suitable biosignal or any other suitable signal.

In some embodiments, signal 816 may be coupled to processor 812. Processor 812 may be any suitable software, firmware, hardware, or combination thereof for processing signal 816. For example, processor 812 may include one or more hardware processors (e.g., integrated circuits), one or more software modules, computer-readable media such as memory, firmware, or any combination thereof. Processor 812 may, for example, be a computer or may be one or more chips (i.e., integrated circuits). Processor 812 may, for example, include an assembly of analog electronic components. Processor 812 may calculate physiological information. For example, processor 812 may compute one or more of a pulse rate, respiration rate, blood pressure, or any other suitable physiological parameter. Processor 812 may perform any suitable signal processing of signal 816 to filter signal 816, such as any suitable band-pass filtering, adaptive filtering, closed-loop filtering, any other suitable filtering, and/or any combination thereof. Processor 812 may also receive input signals from additional sources (not shown). For example, processor 812 may receive an input signal containing information about treatments provided to the subject. Additional input signals may be used by processor 812 in any of the calculations or operations it performs in accordance with processing system 800.

In some embodiments, all or some of pre-processor 820, processor 812, or both, may be referred to collectively as processing equipment. In some embodiments, any of the processing components and/or circuits, or portions thereof, of FIGS. 1, 3, 7, and 8 may be referred to collectively as processing equipment. For example, processing equipment may be configured to amplify, filter, sample and digitize input signal 816 (e.g., using an analog-to-digital converter), and calculate physiological information from the digitized signal. In some embodiments, all or some of the components of the processing equipment may be referred to as a processing module.

Processor 812 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 812 to, for example, store fiducial information or initialization information corresponding to physiological monitoring. In some embodiments, processor 812 may store physiological measurements or previously received data from signal 816 in a memory device for later retrieval. In some embodiments, processor 812 may store calculated values, such as a pulse rate, a blood pressure, a blood oxygen saturation, a fiducial point location or characteristic, an initialization parameter, or any other calculated values, in a memory device for later retrieval.

Processor 812 may be coupled to output 814. Output 814 may be any suitable output device such as a serial port which can interface with many types of devices, or another interface with one or more medical devices (e.g., a medical monitor that displays various physiological parameters, a medical alarm, or any other suitable medical device that either displays physiological parameters or uses the output of processor 812 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 800 may be incorporated into system 100 of FIG. 1 in which, for example, input signal generator 810 may be implemented as part of sensor 102, or into system 710 of FIG. 7 in which, for example, input signal generator 810 may be implemented as part of sensor unit 712 (FIG. 7), and processor 812 may be implemented as part of monitor 104 (FIG. 1) or as part of monitor 714 (FIG. 7). Furthermore, all or part of system 800 may be embedded in a small, compact object carried with or attached to the subject (e.g., a watch, other piece of jewelry, or a smart phone). In some embodiments, a wireless transceiver (not shown) may also be included in system 800 to enable wireless communication with other components of systems 100 and 710 (FIGS. 1 and 7). As such, systems 100 and 710 may be part of a fully portable and continuous subject monitoring solution. In some embodiments, a wireless transceiver (not shown) may also be included in system 800 to enable wireless communication with other components of systems 100 and 710 (FIGS. 1 and 7). For example, pre-processor 820 may output signal 816 over BLUETOOTH, 802.11, WiFi, WiMax, cable, satellite, Infrared, or any other suitable transmission scheme. In some embodiments, a wireless transmission scheme may be used between any communicating components of system 800. In some embodiments, system 800 may include one or more communicatively coupled modules configured to perform particular tasks. In some embodiments, system 800 may be included as a module communicatively coupled to one or more other modules.

It will be understood that the components of signal processing system 800 that are shown and described as separate components are shown and described as such for illustrative purposes only. In other embodiments the functionality of some of the components may be combined in a single component. For example, the functionality of processor 812 and pre-processor 820 may combined in a single processor system. Additionally, the functionality of some of the components shown and described herein may be divided over multiple components. Additionally, signal processing system 800 may perform the functionality of other components not show in FIG. 8. For example, some or all of the functionality of control circuitry 110 of FIG. 1 may be performed in signal processing system 800. In other embodiments, the functionality of one or more of the components may not be required. In an embodiment, all of the components can be realized in processor circuitry.

The foregoing may be merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it may be emphasized that this disclosure may be not limited to the explicitly disclosed methods, systems, and apparatuses, but may be intended to include variations to and modifications thereof which are within the spirit of the following claims.

What is claimed:

1. A method of processing a physiological signal to determine a physiological parameter of a subject, the method comprising:

receiving, using a pulse oximeter, a light signal attenuated by a subject, wherein the light signal comprises a first component corresponding to a desired component and a second component corresponding to an undesired component;

performing, using a pulse oximeter, a first filtering operation on the light signal to remove at least a portion of the undesired component using a first analog filter having a first transfer function to generate a filtered analog signal;

converting, using the pulse oximeter, the filtered analog signal into a digital signal;

performing, using the pulse oximeter, a second filtering operation on the digital signal using a second digital filter having a second transfer function to generate a filtered digital signal, wherein the second transfer function is substantially an inverse of the first transfer function; and determining, using the pulse oximeter, the physiological parameter based on the filtered digital signal.

2. The method of claim 1, wherein the second transfer function includes at least one pole whose position is adjusted in order to stabilize the second filter.

3. The method of claim 1, wherein the first filtering operation introduces an overshoot or droop to the filtered analog signal.

4. The method of claim 3, wherein the second filtering operation at least partially removes the overshoot or droop introduced by the first filtering operation.

5. The method of claim 1, wherein the undesired component comprises ambient light noise.

6. The method of claim 1, further comprising generating a photonic signal comprising at least one wavelength of light, wherein the desired component of the detected light signal corresponds to the photonic signal, wherein the photonic signal comprises a plurality of first segments and a plurality of second segments, wherein light is transmitted during the first segments and no light is transmitted during the second segments, and wherein the first segments and the second segments alternate.

7. The method of claim 1, wherein the first analog filter comprises an analog high pass filter.

8. The method of claim 1, wherein the second digital filter comprises a digital inverse high pass filter.

9. The method of claim 8, wherein the first analog filter comprises an analog high pass filter.

10. The method of claim 1, wherein the physiological parameter comprises one or more of a pulse rate, a respiration rate, and a blood oxygen saturation of the subject.

11. A pulse oximetry system for processing a physiological signal to determine a physiological parameter of a subject, the system comprising:
    a pulse oximetry sensor configured to receive a light signal attenuated by a subject, wherein the light signal comprises a first component corresponding to a desired component and a second component corresponding to an undesired component; and
    a pulse oximeter coupled to the pulse oximetry sensor, wherein the pulse oximeter comprises:
        a first analog filter having a first transfer function, wherein the first analog filter is configured to perform a first filtering operation on the light signal to remove at least a portion of the undesired component to generate a filtered analog signal;
        an analog-to-digital converter configured to convert the filtered analog signal into a digital signal;
        a second digital filter having a second transfer function, wherein the second filter is configured to perform a second filtering operation on the digital signal to generate a filtered digital signal, wherein the second transfer function is substantially an inverse of the first transfer function; and
        a processor configured to determine the physiological parameter based on the filtered digital signal.

12. The system of claim 11, wherein the second transfer function includes at least one pole whose position is adjusted in order to stabilize the second filter.

13. The system of claim 11, wherein the first filter is configured to introduce an overshoot or droop to the filtered analog signal.

14. The system of claim 13, wherein the second filter is configured to at least partially remove the overshoot or droop introduced by the first filter.

15. The system of claim 11, wherein the undesired component comprises ambient light noise.

16. The system of claim 11, further comprising a light source configured to generate a photonic signal comprising at least one wavelength of light, wherein the desired component of the detected light signal corresponds to the photonic signal, wherein the photonic signal comprises a plurality of first segments and a plurality of second segments, wherein light is transmitted during the first segments and no light is transmitted during the second segments, and wherein the first segments and second segments alternate.

17. The system of claim 11, wherein the first analog filter comprises an analog high pass filter.

18. The system of claim 11, wherein the second digital filter comprises a digital inverse high pass filter.

19. The system of claim 18, wherein the first analog filter comprises an analog high pass filter.

20. The system of claim 11, wherein the physiological parameter comprises one or more of a pulse rate, a respiration rate, and a blood oxygen saturation of the subject.

21. A method of processing a physiological signal to determine a physiological parameter of a subject, the method comprising:
    receiving, using a pulse oximeter, a light signal attenuated by a subject, wherein the light signal comprises a first component corresponding to a desired component and a second component corresponding to an undesired component;
    performing, using a pulse oximeter, a first filtering operation on the light signal to remove at least a portion of the undesired component using a first analog filter to generate a first filtered signal, wherein the first filtering operation introduces a distortion to the first filtered signal;
    converting, using the pulse oximeter, the first filtered signal into a digital signal;
    performing, using a pulse oximeter, a second filtering operation on the digital signal to remove at least a portion of the distortion using a second digital filter to generate a second filtered signal; and
    determining, using the pulse oximeter, the physiological parameter based on the second filtered signal.

* * * * *